United States Patent
O'Lenick, Jr. et al.

(10) Patent No.: US 7,157,104 B1
(45) Date of Patent: Jan. 2, 2007

(54) GUERBET CRANBERRY ESTERS AS A DELIVERY SYSTEM FOR NATURAL ANTIOXIDANTS

(75) Inventors: Anthony J. O'Lenick, Jr., Dacula, GA (US); Carter LaVay, Riverside, CT (US)

(73) Assignee: Zenitech LLC, Old Greenwich, CT (US)

( * ) Notice: Subject to any disclaimer, the term of this patent is extended or adjusted under 35 U.S.C. 154(b) by 489 days.

(21) Appl. No.: 10/444,470

(22) Filed: May 27, 2003

(51) Int. Cl.
*A01N 65/00* (2006.01)

(52) U.S. Cl. .................................................. 424/725

(58) Field of Classification Search ................. 424/725
See application file for complete search history.

(56) References Cited

U.S. PATENT DOCUMENTS

| | | | |
|---|---|---|---|
| 4,868,236 A | 9/1989 | O'Lenick | |
| 5,488,121 A | 1/1996 | O'Lenick | |
| 2003/0099604 A1* | 5/2003 | Light | 424/64 |
| 2004/0180032 A1* | 9/2004 | Manelski et al. | 424/70.121 |

\* cited by examiner

*Primary Examiner*—Michael Meller

(57) ABSTRACT

The present invention relates to Cranberry seed oil derivatives derived by the reaction of a guerbet alcohol and cold pressed Cranberry seed oil. The choice of cold pressed Cranberry seed oil as a raw material in the preparation of the compounds of the present invention is critical, since it has been found that the cold pressed Cranberry seed oil contains antioxidants, antimicrobial compounds and which when reacted with a guerbet alcohol result in products that deliver said actives to the skin and hair, resulting in protection of the skin and hair from environmental factors such as acid rain, ozone attack and UV degradation.

15 Claims, No Drawings

GUERBET CRANBERRY ESTERS AS A DELIVERY SYSTEM FOR NATURAL ANTIOXIDANTS

BACKGROUND OF THE INVENTION

The present invention relates to cranberry seed oil derivatives derived by the reaction of specific beta branched alcohols, referred to as guerbet alcohols and cold pressed cranberry seed oil. The choice of cold pressed cranberry seed oil as a raw material in the preparation of the compounds of the present invention is critical, since it has been found that the cold pressed cranberry seed oil contains a unique antioxidant which when reacted with a guerbet alcohol result in products that deliver said actives to the skin and hair, resulting in protection of the skin and hair from environmental factors such as acid rain, ozone attack and UV degradation.

U.S. Pat. No. 6,391,345 issued May 2002 describes the refining of cold pressed cranberry seed oil, and is incorporated herein by reference. American cranberries, Vaccinium macrocarpon, are native plants of open, acid peat bogs in North America. Cranberry plants are evergreen perennial vines that produce runners and upright branches with terminal flower buds.

Cranberries have historically been harvested and either ingested as whole berries, such as in cranberry sauce, or have been processed for their juice. Pulp remaining after cranberry juice extraction processing has historically been regarded as an undesirable waste product with little or no utility.

In the United States, cranberries are grown and are harvested in the Northeast, Northwest and Great Lakes regions. Cranberries ripen and are harvested in autumn, which has made cranberries a holiday food. Cranberries have not changed significantly in appearance and nutritional value over time. Cranberries have typically been stored by freezing or drying the whole berries.

Cranberries have become a popular food only in recent years because cranberries have a very bitter taste. Historically, processors have not dealt well with the taste. Cranberries are known to contain quininic acid. It is the quininic acid that imparts to cranberries, the bitter taste. Cranberry juice has become more palatable because it is blended with other sugar-containing aqueous liquids.

Apart from an undesirable taste, quininic acid is believed to have nutraceutical properties. When ingested, quininic acid is converted to hippuric acid. Hippuric acid is believed to remove toxins from the bladder, kidneys, prostate and testicles. Under normal circumstances, oils useful in the cosmetic industry are refined with a variety of steps that are designed to maximize triglyceride content, and minimize color and odor. These steps include steam distillation, a process in which steam is sparged through the oil to remove odor and color bodies and solvent extraction with compounds like hexane, which remove additional odor and color bodies. We have learned that these processes, while improving color and odor, remove many of the desirable "active" materials like tocopherols, antioxidants and the like. What results is a light color, low odor triglyceride with no appreciable added skin benefits. We have surprisingly learned that when the cranberry seed oil that is cold processed is reacted with specific water-soluble silicone compounds, the actives (normally removed in non-cold press process) remain in the product, become water-soluble and have outstanding activity on the skin. In essence two things happen when the cold pressed cranberry seed oil is reacted with dimethicone copolyol. First the triglyceride reacts with the hydroxyl group of the silicone compound, giving a water-soluble ester. Secondly, the water-soluble ester solubilized the active components there as a consequence of cold pressing. Thirdly, these very desirable materials are deposited on the skin by the silicone fatty ester, based upon its proclivity to remain on the skin. The result is a unique delivery of the actives to the skin from totally natural fruit oil.

Guerbet alcohols have been known for many years, primarily for their liquidity at high molecular weight. Over the years there have been a number of derivatives patented. U.S. Pat. No. 4,868,236 to O'Lenick discloses a guerbet citric ester and polymers thereof useful in plastic lubrication. U.S. Pat. No. 5,488,121 issued Jan. 30, 1996 to O'Lenick teaches that esters based upon a guerbet acid and guerbet alcohol have surprisingly good liquidity. However these patents did not disclose or suggest the possibility of using cold pressed cranberry seed oil that is rich in antioxidants and other actives that could be delivered to the skin using a specific silicone ester as a delivery molecule.

SUMMARY OF THE INVENTION

The present invention relates to a series of guerbet esters derived from the reaction of cold pressed Cranberry oil and specific guerbet alcohols.

The present invention also relates to a process of treating hair and skin, which comprises contacting the hair and skin with an effective anti-oxidant containing amount of a Cranberry guerbet ester of the preset invention.

DETAILED DESCRIPTION OF THE INVENTION

We have found that cranberry oil prepared by a cold press extraction process described in U.S. Pat. No. 6,391,345 issued May 2002, contain specific antioxidant materials that are removed by more aggressive refining processes like solvent extraction. These compounds surprisingly survive the reaction with guerbet alcohols and result in a water-soluble delivery system for these very desirable natural compounds.

Also critical to the practice of the present invention is the fatty composition of the cold pressed cranberry oil. This cranberry oil has a substantially clear appearance with a pale yellow color.

Cold Pressed Cranberry Oil is a triglyceride conforming to the following structure:

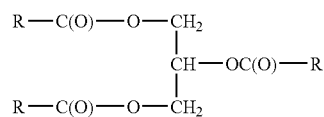

The R—C(O)— group has the following composition:

| Component | % Weight |
| --- | --- |
| 16:0 palmitic | 5.0 to 6.0 |
| 18:0 stearic | 1.0 to 2.0 |
| 18:1 oleic | 20 to 25 |
| 18:2 linoleic | 35 to 40 |
| 18:3 linolenic (alpha) | 30 to 35 |
| 20:0 arachidic | 0.13 |

-continued

| Component | % Weight |
|---|---|
| 20:1 gadoleic | 0.20 |
| 20:5 (n-3) | 0.32 |
| 22:2 | 1.1 |
| Myristic | 0.01 |
| Pentadecanoic | 0.02 |
| Palmitoleic (trans) | 0.13 |
| Palmitoleic (cis) | 0.08 |
| 10-heptadecanoic | 0.03 |
| Gamma linolenic | 0.1 to 0.2 |
| Nonadecanoic | 0.1 to 0.2 |
| 11-transeicosenic | 0.22 |
| 11, 14 eicosandienoic | 0.1 |
| 11, 14, 17 cicosatrienoic | 0.01 |
| Eicosapentaenoic | 0.01 |
| Behenic | 0.03 |
| Erucic | 0.02 |
| Docosapentacnoic | 0.01 |
| Tricosanoic | 0.01 |
| Lignoceric | 0.02 |
| Nervonic | 0.02 |

The oil also contains the following very critical "active" components for skin and hair care:

| Compound | mg/kg |
|---|---|
| Campesterol/brassicasterol (mg/kg) | 66.0 |
| Stigmasterol (mg/kg) | 68.0 |
| Beta-sitosterol (mg/kg) | 1319.0 |
| Phosphatidylinositiol (mg/kg) | 9.9 |
| Phosphatidylcholine (mg/kg) | 202.0 |
| Alpha-tocopherol (mg/kg) | 341.0 |
| Gamma-tocopherol (mg/kg) | 110.0 |

When the oil is exposed to steam strip and solvent extraction the concentration of the "active" components drops to vanishingly small levels and the activity is lost.

As can be seen, the cold pressed cranberry seed oil is a rich source of compounds having important properties when applied to hair and skin. Stigmasterol is an anti-stiffness factor. Beta-sitosterol has use as an antihyperlipoproteinemic agent. One or more of the campesterol, stigmasterol and beta-sitosterol has inflammatory activity and may be useful in the treatment of gingivitis, rash, eczema, and other skin lesions. It is also believed that these compounds found in cranberry seed oil have activity as sunscreen agents. Since some of the compounds present in cranberry oil have absorbance in the UV-B range. It is this range that causes the greatest cellular damage. The cold pressed cranberry oil can shield against UV-A induced damage by scattering light as well as by light spectrum absorption. The cold pressed cranberry oil has, then activity as a broad spectrum UV protectant. The cranberry oil may be used alone or in combination with other conventional sunscreens. (emphasis added)

The phosphatidylinositiol and phosphatidylcholine and tocopherols are highly desirable materials used on skin. The phosphatidylcholine, also known as lecithin, is found in human beings in the nervous system and the brain. Lecithin also has use as an edible and digestible surfactant. It is usable in manufacturing foods such as margarine and chocolate. Lecithin is a natural antioxidant that can increase oil stability and shelf life. Lecithin also has use in pharmaceuticals, cosmetics, skin care, and in treating leather and textiles.

Cold pressed cranberry seed oil has a very high concentration of gamma tocopherol. This level is much higher than is found in oils such as safflower and grape, which are 11 and 33, respectively. The gamma tocopherol has the most antioxidant capacity of all of the tocopherols and contributes to the stability of highly unsaturated oils in the cranberry oil. It is believed that the presence of the high gamma tocopherol concentration makes cranberry oil an excellent additive to animal food-both human and non-human. The gamma tocopherol may be as important as alpha tocopherol in preventing degenerative diseases.

Cold pressed cranberry seed oil has a high linolenic acid content. Linolenic acid has been implicated as a food additive and nutraceutical in preventing coronary heart disease and cancer. Cranberry oil also has a high polyunsaturated: saturated ratio in a neutral lipid fraction, of 10:1. This ratio is regarded as having value in reducing serum cholesterol, atherosclerosis and in preventing heart disease.

Cold pressed cranberry seed oil has a rather dark yellow to orange color because it contains carotenoids. The carotenoids are usable as colorant substitutes for materials such as carotenes, annotos, and apocarotenals used in the nutraceutical and oil industries.

The ability to make derivatives of the oil in which the protection of the components of the cold pressed oil remain functional is a major aspect of the present invention.

Cold pressed Cranberry seed oil has a very high concentration of gamma tocopherol. This level is much higher than is found in oils such as safflower and grape, which are 11 and 33, respectively. The gamma tocopherol has the most antioxidant capacity of all of the tocopherols and contributes to the stability of highly unsaturated oils in the Cranberry oil. It is believed that the presence of the high gamma tocopherol concentration makes Cranberry oil an excellent additive to animal food-both human and non-human. The gamma tocopherol may be as important as alpha tocopherol in preventing degenerative diseases.

Cold pressed Cranberry seed oil has a high linolenic acid content. Linolenic acid has been implicated as a food additive and nutraceutical in preventing coronary heart disease and cancer. Cranberry oil also has a high polyunsaturated: saturated ratio in a neutral lipid fraction, of 10:1. This ratio is regarded as having value in reducing serum cholesterol, atherosclerosis and in preventing heart disease.

Cold pressed Cranberry seed oil has a rather dark yellow to orange color because it contains carotenoids. The carotenoids are usable as colorant substitutes for materials such as carotenes, annotos, and apocarotenals used in the nutraceutical and oil industries.

The cold pressed Cranberry seed oil, containing all of the above desirable compounds, is reacted with a guerbet alcohol conforming to the following structure:

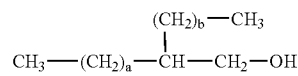

wherein;

a is an integer ranging from 5 to 17;

b is an integer ranging from 3 to 15.

R is derived from cold pressed cranberry seed oil and has the following composition;

| Component | % by Weight of "R" |
|---|---|
| 16:0 palmitic | 5.0 to 6.0 |
| 18:0 stearic | 1.0 to 2.0 |
| 18:1 oleic | 20 to 25 |
| 18:2 linoleic | 35 to 40 |
| 18:3 linolenic (alpha) | 30 to 35 |
| 20:0 arachidic | 0.13 |
| 20:1 gadoleic | 0.20 |
| 20:5 (n-3) | 0.32 |
| 22:2 | 1.1 |
| Myristic | 0.01 |
| Pentadecanoic | 0.02 |
| Palmitoleic (trans) | 0.13 |
| Palmitoleic (cis) | 0.08 |
| 10-heptadecanoic | 0.03 |
| Gamma linolenic | 0.1 to 0.2 |
| Nonadecanoic | 0.1 to 0.2 |
| 11-transeicosenic | 0.22 |
| 11, 14 eicosandienoic | 0.1 |
| 11, 14, 17 eicosatrienoic | 0.01 |
| Eicosapentaenoic | 0.01 |
| Behenic | 0.03 |
| Erucic | 0.02 |
| Docosapentaenoic | 0.01 |
| Tricosanoic | 0.01 |
| Lignoceric | 0.02 |
| Nervonic | 0.02 |

Also present in the product are the following "actives"

Compound

Campesterol/brassicasterol

Stigmasterol

Beta-sitostero

Phosphatidylinositiol

Phosphatidylcholine

Alpha-tocopherol

Gamma-tocopherol

The current invention describes a composition, which is prepared by the reaction esterification reaction of:

(1) cold pressed cranberry seed oil

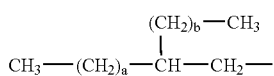

a is an integer ranging from 5 to 17;

b is an integer ranging from 3 to 15.

The current invention describes a composition, which is prepared by the reaction esterification reaction of:

(1) cold pressed Cranberry seed oil (2) a guerbet alcohol conforming to the following structure

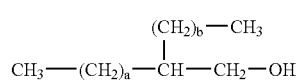

wherein;

a is an integer ranging from 5 to 17;

b is an integer ranging from 3 to 15.

The compounds of the present invention deliver these active products to skin, therefore the invention also discloses a process for conditioning skin which comprises contacting the skin with an effective conditioning concentration of a Cranberry guerbet ester, which conforms to the following structure;

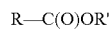

wherein;

R is derived from cold pressed Cranberry seed oil;

R' is;

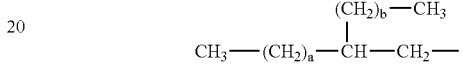

a is an integer ranging from 5 to 17;

b is an integer ranging from 3 to 15. The effective conditioning concentration ranges from 0.01 to 15.0% by weight.

PREFERRED EMBODIMENT

In a preferred embodiment a is 5 and b is 3.
In a preferred embodiment a is 7 and b is 5.
In a preferred embodiment a is 9 and b is 7.
In a preferred embodiment a is 11 and b is 9.
In a preferred embodiment a is 13 and b is 11.
In a preferred embodiment a is 17 and b is 15.

EXAMPLES

The compounds of the present invention are made from commercially available raw materials.

Raw Materials

Cold Pressed Cranberry Seed Oil

Cold Presses Cranberry seed oil is an item of commerce sold by Regal Trade & Consult LLC. of Hoboken, N.J. It is processed using U.S. Pat. No. 6,391,345 issued May 2002.

Guerbet Alcohols

Condea Chemical produces guerbet alcohols commercially. The values of a and b were actually determined by analysis and are not dependant upon trade name for meaning.

| Example | Commercial Name | a | b | Chemical Name |
|---|---|---|---|---|
| 1 | Isofol 12 | 5 | 3 | 2-butyl-octanol |
| 2 | Isofol 16 | 7 | 5 | 2-hexyl-decanol |
| 3 | Isofol 20 | 9 | 7 | 2-octyl-dodecanol |
| 4 | Isofol 24 | 11 | 9 | 2-decyl-tetradecanol |
| 5 | Isofol 28 | 13 | 11 | 2-dodecyl-hexadecanol |
| 6 | Isofol 36 | 17 | 15 | 2-hexadecyl-eicosonol |

General Procedure

To grams of 400 grams of Cold Pressed Cranberry seed oil is added the specified amount of the specified guerbet alcohol (examples –10). Next 0.1% of a suitable esterification catalyst is added. The catalyst is selected from the group consisting of methane sulfonic acid, tin compounds and titinate compounds. The preferred catalyst is dilauryl tin oxide.

The reaction mass is heated to 180–200° C., under good agitation. As the reaction mass is held at temperature, the material clears and becomes homogeneous. The reaction mass is held for eight hours at reaction temperature, then cooled to ambient. Upon standing, the glycerin formed separates into from the product and is removed by decanting. The resulting product is in the other phase and is used without additional purification.

|  | Guerbet Alcohol | |
| --- | --- | --- |
| Example | Example | Grams |
| 11 | 1 | 186.0 |
| 12 | 2 | 242.0 |
| 13 | 3 | 298.0 |
| 14 | 4 | 354.0 |
| 15 | 5 | 410.0 |
| 16 | 6 | 522.0 |

The products of examples 1–3 are liquid at ambient temperatures. The products 4–6 are pastes.

Applications Examples

The compounds of the present invention are oil-soluble compounds that have an extraordinary skin feel and provide antioxidant, and other desirable properties from the components that are not removed from the Cranberry oil when it is cold processed. The cold processing leaves behind the desirable components, which in turn are not destroyed by the reaction and surprisingly, become oil-soluble and delivered to the skin.

In addition to delivering the desirable compounds to the surface of the skin, the compounds are breathable and provide moisturizing and emmoliency to the skin.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains

What is claimed;

1. A cranberry guerbet ester, which conforms to the following structure;

R—C(O)OR' wherein;
R is derived from cold pressed cranberry seed oil;
R' is;

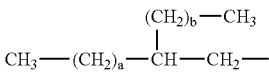

a is an integer ranging from 5 to 17;
b is an integer ranging from 3 to 15, wherein the R—C(O)— group has the following composition:

| Component | % Weight |
| --- | --- |
| 16:0 palmitic | 5.0 to 6.0 |
| 18:0 stearic | 1.0 to 2.0 |
| 18:1 oleic | 20 to 25 |
| 18:2 linoleic | 35 to 40 |
| 18:3 linolenic (alpha) | 30 to 35 |
| 20:0 arachidic | 0.13 |
| 20.1 gadoleic | 0.20 |
| 20:5 (n-3) | 0.32 |
| 22:2 | 1.1 |
| Myristic | 0.01 |
| Pentadecanoic | 0.02 |
| Palmitoleic (trans) | 0.13 |
| Palmitoleic (cis) | 0.08 |
| 10-heptadecanoic | 0.03 |
| Gamma linolenic | 0.1 to 0.2 |
| Nonadecanoic | 0.1 to 0.2 |
| 11-transeicosenic | 0.22 |
| 11, 14 eicosandienoic | 0.1 |
| 11, 14, 17 cicosatrienoic | 0.01 |
| Eicosapentaenoic | 0.01 |
| Behenic | 0.03 |
| Erucic | 0.02 |
| Docosapentaenoic | 0.01 |
| Tricosanoic | 0.01 |
| Lignoceric | 0.02 |
| Nervonic | 0.02. |

2. A cranberry guerbet ester of claim 1 wherein a is 5 and b is 3.

3. A cranberry guerbet ester of claim 1 wherein a is 7 and b is 5.

4. A cranberry guerbet ester of claim 1 wherein a is 9 and b is 7.

5. A cranberry guerbet ester of claim 1 wherein a is 11 and b is 9.

6. A cranberry guerbet ester of claim 1 wherein a is 13 and b is 11.

7. A cranberry guerbet ester of claim 1 wherein a is 17 and b is 15.

8. A process for conditioning skin which comprises contacting the skin with an effective conditioning concentration of a cranberry guerbet ester, which conforms to the following structure;

R—C(O)OR' wherein;
R is derived from cold pressed cranberry seed oil;
R' is;

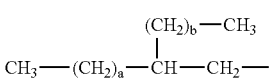

a is an integer ranging from 5 to 17;
b is an integer ranging from 3 to 15, wherein the R—C(O)— group has the following composition:

| Component | % Weight |
| --- | --- |
| 16:0 palmitic | 5.0 to 6.0 |
| 18:0 stearic | 1.0 to 2.0 |
| 18:1 oleic | 20 to 25 |
| 18:2 linoleic | 35 to 40 |
| 18:3 linolenic (alpha) | 30 to 35 |
| 20:0 arachidic | 0.13 |
| 20.1 gadoleic | 0.20 |
| 20:5 (n-3) | 0.32 |
| 22:2 | 1.1 |
| Myristic | 0.01 |
| Pentadecanoic | 0.02 |
| Palmitoleic (trans) | 0.13 |
| Palmitoleic (cis) | 0.08 |
| 10-heptadecanoic | 0.03 |
| Gamma linolenic | 0.1 to 0.2 |
| Nonadecanoic | 0.1 to 0.2 |
| 11-transeicosenic | 0.22 |
| 11, 14 eicosandienoic | 0.1 |
| 11, 14, 17 cicosatrienoic | 0.01 |
| Eicosapentaenoic | 0.01 |
| Behenic | 0.03 |
| Erucic | 0.02 |
| Docosapentaenoic | 0.01 |
| Tricosanoic | 0.01 |
| Lignoceric | 0.02 |
| Nervonic | 0.02. |

9. A process of claim 8 wherein said effective conditioning concentration ranges from 0.01 to 15.0% by weight.

10. A process of claim 9 wherein a is 5 and b is 3.

11. A process of claim 9 wherein a is 7 and b is 5.

12. A process of claim 9 wherein a is 9 and b is 7.

13. A process of claim 9 wherein a is 11 and b is 9.

14. A process of claim 9 wherein a is 13 and b is 11.

15. A process of claim 9 wherein a is 17 and b is 15.

* * * * *